(12) United States Patent
Koay et al.

(10) Patent No.: US 11,510,712 B2
(45) Date of Patent: Nov. 29, 2022

(54) PROXIMAL FEMUR PLATE SYSTEM

(71) Applicant: DePuy Synthes Products, Inc., Raynham, MA (US)

(72) Inventors: Kenny Koay, West Chester, PA (US); Jessica Galie, West Chester, PA (US); Troy Probst, West Chester, PA (US); Peter Fatone, West Chester, PA (US); Bryan Fritz, West Chester, PA (US); Mike Brace, West Chester, PA (US); Glenna Smith, West Chester, PA (US); George J. Haidukewych, Orlando, FL (US); Karl Stoffel, Bottmingen (CH); Cory A. Collinge, Fort Worth, TX (US); Frank A. Liporace, Fort Worth, TX (US); Bruce H. Ziran, Atlanta, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/918,655

(22) Filed: Mar. 12, 2018

(65) Prior Publication Data

US 2018/0256220 A1   Sep. 13, 2018

Related U.S. Application Data

(60) Provisional application No. 62/470,753, filed on Mar. 13, 2017, provisional application No. 62/470,766, filed on Mar. 13, 2017.

(51) Int. Cl.
  *A61B 17/74*   (2006.01)
  *A61B 17/80*   (2006.01)
(52) U.S. Cl.
  CPC ............ *A61B 17/742* (2013.01); *A61B 17/74* (2013.01); *A61B 17/80* (2013.01);
  (Continued)

(58) Field of Classification Search
  CPC ....... A61B 17/74; A61B 17/742; A61B 17/80; A61B 17/8004; A61B 17/8057; A61B 17/8061
  See application file for complete search history.

(56) References Cited

U.S. PATENT DOCUMENTS

| 4,565,193 A | 1/1986 | Streli |
| 4,973,332 A | 11/1990 | Kummer |
(Continued)

FOREIGN PATENT DOCUMENTS

| FR | 3010300 | 3/2015 |
| JP | 2005-537087 A | 12/2005 |
(Continued)

*Primary Examiner* — Kevin T Truong
*Assistant Examiner* — Tracy L Kamikawa
(74) *Attorney, Agent, or Firm* — BakerHostetler (57) ABSTRACT

A bone plate for treating periprosthetic fractures includes a head portion sized and shaped so that, in an operative position, a proximal end thereof aligns with a vastus ridge of a greater trochanter of a femur. The plate also includes a shaft portion extending distally from the head portion. The shaft portion includes offset holes to receive bone fixation elements therethrough. Each of the offset holes includes a first hole positioned on a first side of a longitudinal axis of the plate and a second hole positioned on a second side of the longitudinal axis opposite the first side so that bone fixation elements inserted therethrough extend anterior and posterior of a prosthetic received within the femur. The first and second holes are staggered relative to one another along a length of the shaft portion and extending beyond longitudinal edges of the shaft portion.

20 Claims, 6 Drawing Sheets

(52) U.S. Cl.
CPC ...... *A61B 17/8004* (2013.01); *A61B 17/8057* (2013.01); *A61B 17/8061* (2013.01)

(56) References Cited

U.S. PATENT DOCUMENTS

| | | | |
|---|---|---|---|
| 5,190,545 | A | 3/1993 | Corsi et al. |
| 6,066,141 | A | 5/2000 | Dall et al. |
| 6,338,734 | B1 | 1/2002 | Burke et al. |
| 7,207,993 | B1 | 4/2007 | Baldwin et al. |
| 7,229,444 | B2 | 6/2007 | Boyd |
| 7,255,701 | B2 | 8/2007 | Allen et al. |
| 7,335,204 | B2 | 2/2008 | Tornier |
| 7,951,176 | B2 | 5/2011 | Grady et al. |
| 8,062,296 | B2 | 11/2011 | Orbay et al. |
| 8,142,434 | B2 | 3/2012 | Bluechel |
| 8,197,521 | B2 * | 6/2012 | Sixto, Jr. ............... A61B 17/17 606/283 |
| 8,267,972 | B1 | 9/2012 | Gehlert |
| 8,394,130 | B2 * | 3/2013 | Orbay ............... A61B 17/8057 606/280 |
| 8,728,080 | B2 | 5/2014 | Boomer et al. |
| 8,728,082 | B2 | 5/2014 | Fritzinger et al. |
| 8,764,809 | B2 | 7/2014 | Lorenz et al. |
| 8,795,342 | B2 | 8/2014 | Reisberg |
| 8,808,333 | B2 * | 8/2014 | Kuster ............... A61B 17/74 606/280 |
| 8,834,532 | B2 * | 9/2014 | Velikov ............... A61B 17/80 606/280 |
| 8,894,693 | B2 | 11/2014 | Petit et al. |
| 9,138,267 | B2 * | 9/2015 | Cavallazzi ............. A61B 17/74 |
| 9,283,010 | B2 | 3/2016 | Medoff et al. |
| 2006/0217722 | A1 | 9/2006 | Dutoit et al. |
| 2006/0235401 | A1 | 10/2006 | Baldwin et al. |
| 2007/0270849 | A1 | 11/2007 | Orbay et al. |
| 2010/0262194 | A1 * | 10/2010 | Wagner ............... A61B 17/80 606/286 |
| 2013/0211461 | A1 | 8/2013 | Christen |
| 2014/0243837 | A1 | 8/2014 | Mebarak |
| 2014/0243906 | A1 | 8/2014 | Cavallazzi et al. |
| 2015/0127011 | A1 | 5/2015 | Dunlop et al. |
| 2015/0157373 | A1 | 6/2015 | Wolf et al. |
| 2016/0166298 | A1 | 6/2016 | Mighell et al. |
| 2017/0252080 | A1 * | 9/2017 | Steinhauer ......... A61B 17/8061 |

FOREIGN PATENT DOCUMENTS

| | | |
|---|---|---|
| JP | 2007-506452 A | 3/2007 |
| JP | 2007-289698 A | 11/2007 |
| JP | 2008-532709 A | 8/2008 |
| JP | 2011-502641 A | 1/2011 |
| JP | 3177020 U | 7/2012 |
| JP | 2016-540576 A | 12/2016 |
| WO | 2007103333 | 9/2007 |
| WO | 2011003494 | 1/2011 |
| WO | 2015/088760 | 6/2015 |

* cited by examiner

PROXIMAL FEMUR PLATE SYSTEM

PRIORITY CLAIM

This present application claims priority to U.S. Provisional Patent Application Ser. Nos. 62/470,753 and 62/470,766 both filed on Mar. 13, 2017 the entire disclosure of both is expressly incorporated herein by reference.

BACKGROUND

Proximal femur fractures may be treated with bone plates positioned along the femur to extend across a fracture site. In some cases, however, particularly for periprosthetic fractures, fixation of the bone plate may be difficult as bone fixation elements must be inserted through the bone without interfering with a stem of a previously implanted THA (Total Hip Arthroplasty) system or other intramedullary device.

SUMMARY

The present embodiments are directed to a bone plate for treating periprosthetic fractures, comprising a head portion sized and shaped so that, in an operative position, a proximal end thereof aligns with a vastus ridge of a greater trochanter of a femur and a shaft portion extending distally from the head portion, the shaft portion including pairs of offset holes extending through the shaft portion to receive bone fixation elements therethrough, each of the pairs of offset holes including a first hole positioned on a first side of a longitudinal axis of the bone plate and a second hole positioned on a second side of the longitudinal axis opposite the first side so that bone fixation elements inserted therethrough extend anterior and posterior of a prosthetic received within the femur, the first and second holes staggered relative to one another along a length of the shaft portion and extending beyond longitudinal edges of the shaft portion.

BRIEF DESCRIPTION

DETAILED DESCRIPTION

The present invention may be understood with respect to the following description and the appended drawings, wherein like elements are referred to with the same reference numerals. The present invention relates to the treatment of bone fractures and, in particular, relates to the treatment of periprosthetic proximal femur fractures. Exemplary embodiments describe a modular fixation system comprising a proximal femur plate which may be coupled to a greater trochanter attachment plate and/or a locking attachment plate to treat periprosthetic fractures of the proximal femur. The proximal femur plate includes a head portion configured to be positioned just below the greater trochanter and a shaft portion extending distally therefrom to be positioned along a proximal length of the femur. The proximal femur plate includes pairs of offset holes, a first one of the holes positioned on a first side of a longitudinal axis of the plate and a second one of the holes positioned on a second side of the longitudinal axis, so that, bone fixation elements may be placed on both an anterior side and a posterior side of the prosthetic (e.g., THA stem). Each of the holes extends from a longitudinal side of the proximal femur plate to prevent bone fixation elements inserted therethrough from interfering with the intramedullary implant. The system may further comprise a greater trochanter attachment plate configured to be coupled to the proximal femur plate to provide fixation of the greater trochanter and/or a locking attachment plate coupleable to the proximal femur plate to provide further fixation along the shaft portion of the proximal femur plate. It should be noted that the terms "proximal" and "distal" are intended to a direction relative to the bone on which the system is to be placed. For example as understood by those skilled in the art, in regard to the femur proximal refers to a direction toward a hip joint while distal refers to a direction toward the knee.

Figure 1:
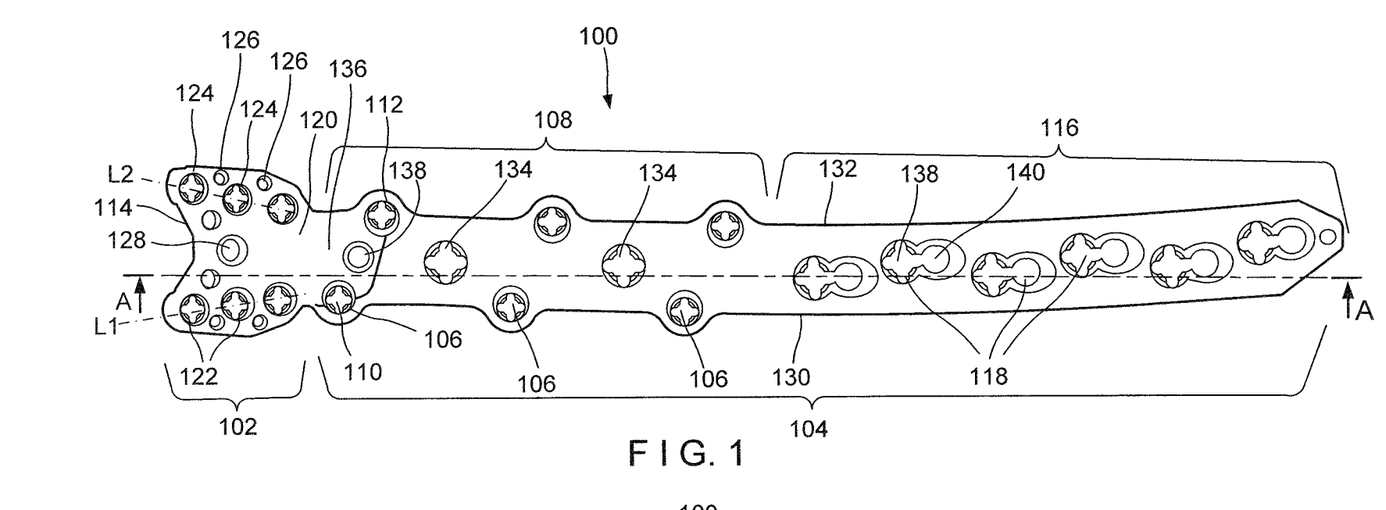
FIG. 1 shows a top plan view of a proximal femur plate according to an exemplary embodiment of the present disclosure.
Figure 2:
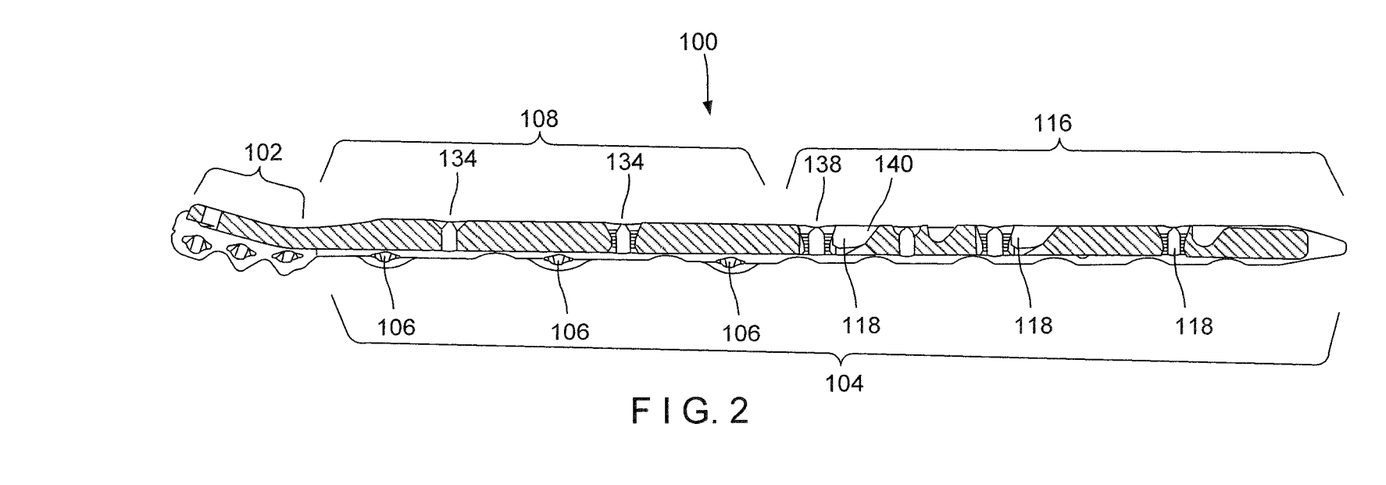
FIG. 2 shows a longitudinal cross-sectional view of the proximal femur plate of FIG. 1, along line A-A.
Figure 3:
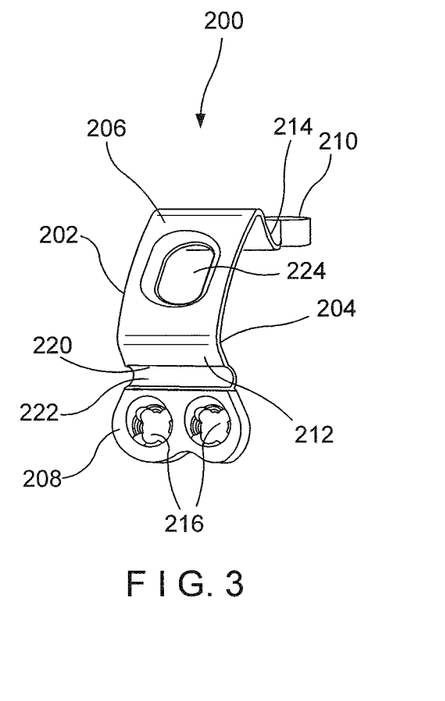
FIG. 3 shows a perspective view of a locking attachment plate coupleable to the proximal femur plate of FIG. 1, according to an exemplary embodiment of the present disclosure.
Figure 4:
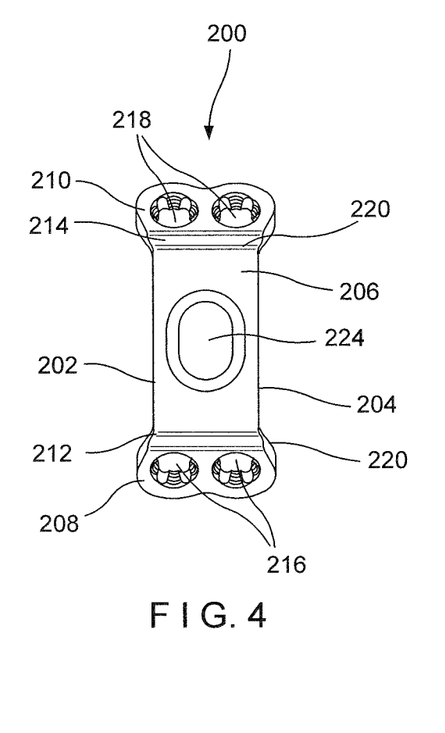
FIG. 4 shows a top plan view of the locking attachment plate of FIG. 3.
Figure 5:
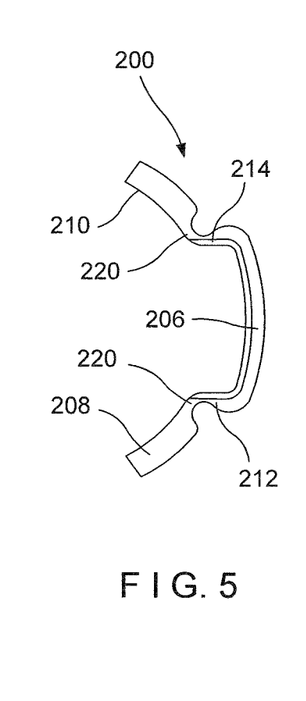
FIG. 5 shows a side view of the locking attachment plate of FIG. 3.

FIGS. 1-11 show a system for treating periprosthetic fractures. The system comprises a proximal femur plate 100, as shown in FIGS. 1-2, which may be used to treat, for example, Vancouver Type B fractures in the proximity of a stem of a previously placed THA prosthetic or other intramedullary device. The proximal femur plate 100 includes a head portion 102 configured to be positioned just below the greater trochanter of a femur and a shaft portion 104 extending therefrom to be positioned along a shaft of the femur. The shaft portion 104 includes pairs of offset holes 106 along the shaft portion 104. Each pair includes a first hole 110 on a first side of the longitudinal axis and a second hole 112 on a second side of the longitudinal axis opposite the first side so that bone fixation elements may be inserted through first and second holes 110, 112 on opposite sides of the THA to provide fixation on both an anterior side of the prosthetic and a posterior side of the prosthetic. The first and second holes 110, 112 are offset or staggered relative to one another along a length of the shaft portion 104 to prevent stress risers in the bone. A locking attachment plate 200, as shown in FIGS. 3-5, may be mounted over the shaft portion 104 of the proximal femur plate 100, between adjacent pairs of offset holes 106, to provide additional fixation openings, if so desired. A greater trochanteric (GT) attachment plate 300, as shown in FIGS. 6-8, 12 and 13, may be coupled to the head portion 102 of the proximal femur plate 100, to provide fixation of, for example, Vancouver Type A fractures in the greater trochanter. The proximal femur plate 100 may be coupled with the locking attachment plate 200 and/or the GT attachment plate 300 or 400 in a modular fashion to provide targeted fixation designed to treat a patient's specific fracture pattern. Although the proximal femur plate 100 is described as being coupled to the locking attachment plate 200 and/or the GT attachment plate 300, it will be understood by those of skill in the art that the proximal femur plate 100 may be used alone to treat femur fractures along a proximal length thereof.

As shown in FIGS. 1-2, the proximal femur plate 100 according to an exemplary embodiment of the present disclosure, includes the head portion 102 which, in an operative position, is configured to be positioned just below the greater trochanter, in line with the lesser trochanter on an opposing side thereof, so that a proximal end 114 of the head portion 102 is aligned with the vastus ridge of the femur (i.e., the inferior border of the greater trochanter). The shaft portion 104 extends distally from the head portion 102 to be positioned along a proximal length of the femur and includes the pairs of offset holes 106. In one embodiment, the shaft portion 104 may include a proximal portion 108 through which the pairs of offset holes 106 extend and may further include a distal portion 116 including a plurality of fixation holes 118 therealong for fixing the distal portion 116 of the shaft portion 104 to the bone. The proximal femur plate 100 may be curved about a longitudinal axis of the femur plate 100 and a length of the shaft 104 may extend along a slight curve relative to the longitudinal axis to correspond to a shape of a femur along which the proximal femur plate 100 is to be positioned. The head portion 102 and the shaft 104 may be slightly angled with respect to one another to correspond to a shape of the femur at a point at which the greater trochanter meets the shaft of the femur.

The head portion 102 extends from the proximal end 114 to a distal end 120 connected to the shaft portion 104. The proximal end 114 in this embodiment includes a curve corresponding generally to a curvature of the vastus ridge so that the proximal femur plate 100 may be positioned in line therewith. The head portion 102 includes a first set of holes 122 extending through the head portion 102 on a first side of the longitudinal axis of the proximal femur plate 100 and a second set of holes 124 extending through the head portion 102 on a second side of the longitudinal axis opposite the first side. The first and second set of holes 122, 124 may be configured to receive bone fixation elements for fixing the head portion 102 to the bone. In one exemplary embodiment, each hole of the first and second set of holes 122, 124 may be configured as variable angles holes so that, a bone fixation element may be inserted therethrough along an axis at an angle within a permitted range of angulations relative to a central axis thereof. It will be understood by those of skill in the art, however, that the holes of the first and second set of holes 122, 124 may have any of a variety of configurations so long as the holes 122, 124 are configured to receive bone fixation elements therethrough. For example, the first and second set of holes 122, 124 may include locking holes. Central axes of the locking holes may be selected to permit bone fixation elements to be inserted therethrough without interfering with any portion of the intramedullary implant. In one exemplary embodiment, the holes 122, 124 may be configured to receive 3.5 mm holes which, as will be recognized by those of skill in the art, have not been widely used in the femur since general trauma plates, which have customarily been used to treat fractures regardless of whether the fractures are periprosthetic fractures, generally include larger holes. Smaller holes may be more desirable for periprosthetic and osteoporotic fractures, however, since there is less bone through which the bone fixation elements may be inserted—e.g., bone not taken up by any portion of the THA implant.

Corresponding ones of the first and second set of holes 122, 124 may be aligned relative to one another along a length of the head portion. A first axis L1 extending through central axes of each of the first set of holes 122 may taper from the proximal end 114 of the head portion 102 toward the distal end 120. Similarly, a second axis L2 extending through central axes of each of the second set of holes 124 may taper from the proximal end 114 toward the distal end 120. In other words, the proximal-most one of the first holes 122 is separated from the proximal-most one of the second holes 124 by a distance greater than a distance separating the distal-most first hole 122 and the distal-most second hole 124. First and second axes L1, L2 in this embodiment taper from the proximal end 114 toward the distal end 120 relative to the longitudinal axis of the proximal femur plate 100 so that, when the plate 100 is positioned along the femur in the operative position, the first and second axes substantially corresponds to a tapering generally found in the stems of intramedullary implants. For example, the taper angle between L1 and L2 may be between 1° and 40°. One exemplary embodiment includes three first holes 122 and three corresponding second holes 124 includes. It will be understood by those of skill in the art, however, that the device may include any desired number of first and second holes 122, 124.

Figure 9:
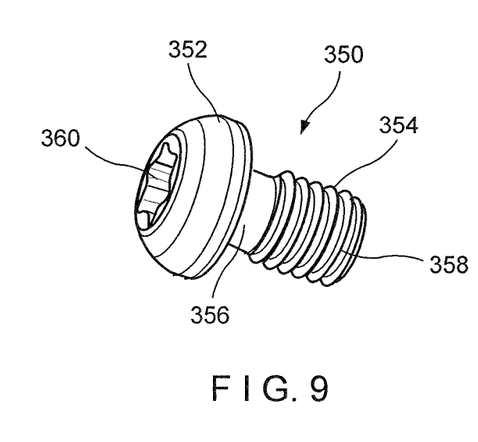
FIG. 9 shows a perspective view of a connecting screw for connecting the greater trochanteric attachment plate of FIG. 6 with the proximal femur plate of FIG. 1.
Figure 10:
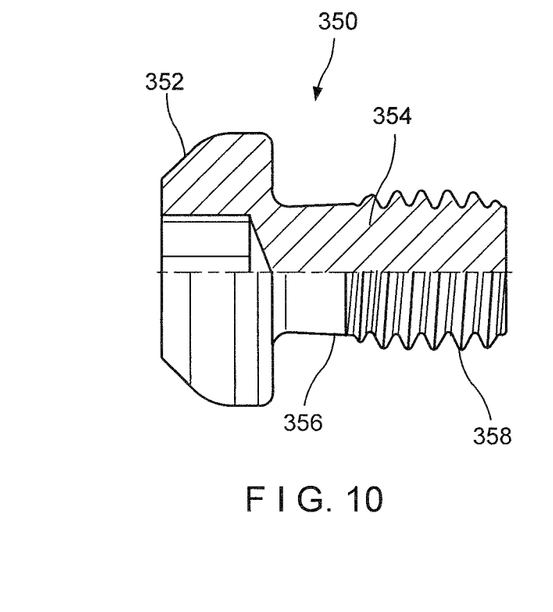
FIG. 10 shows a longitudinal cross-sectional view of the connecting screw of FIG. 9.
Figure 11:
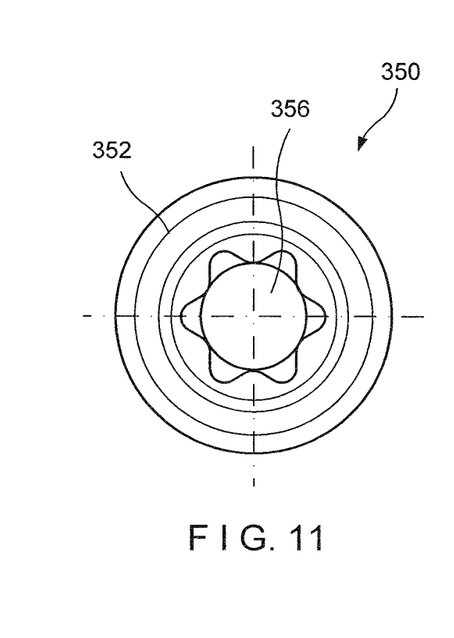
FIG. 11 shows a top plan view of the connecting screw of FIG. 9.

The head portion 102 may further include a plurality of suture openings 126, each of the suture openings 126 being configured to receive a suture therethrough when suturing surrounding tissue to the proximal femur plate 100. In addition, the head portion 102 includes a first GT attachment opening 128 sized and shaped to receive a connecting screw 350, as shown in FIGS. 9-11, when coupling the GT attachment plate 300 to the proximal femur plate 100, as will be described in further detail below. The first GT attachment opening 128 may be threaded for engaging a threading of the connecting screw 350.

The shaft portion 104 extends distally from the distal end 120 of the head portion 102. As described above, the shaft portion 104 includes a proximal portion 108 including the pairs of offset holes 106 and the distal portion 116 including the fixation holes 118. In the operative position, the proximal portion 108 extend along a portion of the femur through which, for example, the stem of the THA prosthetic extends. Each pair of offset holes 106 includes the first hole 110 extending through the shaft portion 104 on the first side of the longitudinal axis and the second hole 112 extending through the shaft portion 104 on the second side of the longitudinal axis opposite the first side so that bone fixation elements are insertable therethrough along both an anterior side and a posterior side of the stem of the prosthetic. The first and second holes 110, 112 are also staggered relative to the length of the shaft portion to minimize stress risers. In one embodiment, the second hole 112 (e.g., a one of the holes 110, 112 on a posterior side of the prosthetic in the operative position) may be positioned distally of the first hole 110 since, in some cases, it has been found that a posterior aspect of the femur has better bone quality. Corresponding holes 110, 112 will, in exemplary embodiments, be offset from one another by a distance of 5 to 15 mm so that an axis connecting center points of the first hole 110 with a center point of its corresponding second hole 112 will form an angle of approximately 16.4° to 41.4° with the longitudinal axis of the plate 100. It may be desired to have holes along the posterior aspect lower (i.e., more distal) so that bone fixation elements may be inserted through better quality bone, lower on the bone where a cross-sectional area of the stem is smaller, maximizing a fixation of the proximal femur plate 100 to the bone.

The first and second holes 110, 112 of each of the pair of offset holes 106 extend beyond first and second longitudinal edges 130, 132, respectively, of the shaft portion 104 to allow for a plate having a smaller width (e.g., distance between longitudinal edges in the portions of the shaft 104 between adjacent first holes 110 and between adjacent second holes 112) than customary trauma plates and to increase the chances of getting around the stem prosthetic. In one embodiment, central axes of the first and second holes 110, 112 may be aligned with the longitudinal edges 130, 132 of the shaft portion 104. A distance between adjacent pair of offset holes 106 is selected to permit a locking attachment plate 200, as shown in FIGS. 3-5, to be mounted thereover, without interfering with either of the first and second holes 110, 112 of each pair of offset holes 106. In other words, a distal one of the first and second holes 110, 112 of a first pair of offset holes 106 should be separated from a proximal one of the first and second holes 110, 112 of a second, adjacent pair of offset holes 106 by a distance of at least a length of the locking attachment plate 200 so that the plate 200 can be placed over the reduced width portion of the plate between adjacent first holes 110 on one side of the shaft 104 and between adjacent ones of the second holes 112 on the other side of the shaft 104.

The proximal portion 108 may also include locking attachment openings 134 extending through a portion thereof between adjacent pairs of offset holes 106 for attaching the attachment plate 200 to the proximal femur plate 100, as will be described in greater detail below. Screws or other fixation elements are inserted into a portion of the attachment plate 200 and through the locking attachment openings 134 to fix the attachment plate 200 to the proximal femur plate 100. The locking attachment openings 134 may be configured as variable angle holes or any other hole capable of receiving a fixation element therein. In one embodiment, the proximal portion 108 of the shaft portion 104 may include three (3) pairs of offset holes 106 and two (2) connecting openings 134. It will be understood by those of skill in the art, however, that the number of pairs of offset holes 106 may vary depending on a desired length of the proximal portion 108 (e.g., length of the stem prosthetic) and a length of the locking attachment plate 200. For cases in which the locking attachment opening 134 is not used for coupling the locking attachment plate 200 to the proximal femur plate, a fixation element such as, for example, a variable angle positioning pin may be inserted therein to couple the shaft portion 104 to the bone with a cable. A proximal end 136 of the proximal portion 108 may also include a second GT attachment opening 138 for coupling the GT attachment plate 300 to the proximal femur plate 300 with, for example, the connecting screw 350, as will be described in greater detail below. Similarly to the first GT attachment opening 128, the second GT attachment opening 138 may be threaded to engage a threading of the connecting screw 350.

The distal portion 116 of the shaft portion 104, in the operative position, may extend along a portion of the femur distal of the stem of the prosthetic. The distal portion 116 includes a plurality of fixation openings 118 along a length thereof. In one embodiment, one or more of the fixation openings 118 may be offset laterally with respect to the longitudinal axis of the shaft portion 104. In other words, central axes along which the fixation openings 118 extend through the distal portion 116 may extend parallel to the longitudinal axis, on either side thereof. The fixation openings 118, however, do not extend beyond either of the first and second longitudinal edges 130, 132 since bone fixation elements inserted therethrough are not required to extend to the side of a prosthetic. In one embodiment, the fixation openings 118 may be configured as combination holes including a first portion 140 configured as a variable angle opening and a second portion 142 being configured as a compression opening. Thus, various bone fixation elements such as, for example, variable angle locking screws, compression screws, and variable angle positioning pins with cables may be inserted into the fixation openings 118. Although the exemplary embodiments of the proximal femur plate 100 are described and shown as including proximal and distal portions 108, 116, the proximal femur plate 100 may also be manufactured as a short plate having a proximal portion 108 with the pairs of offset holes 106 extending therethrough and an elongated combination hole formed on a part extending distally from the proximal part as described in more detail below.

As shown in FIGS. 3-5, the locking attachment plate 200 extends from a proximal end 202 to a distal end 204 along a longitudinal axis of the attachment plate 200 and is configured to be mounted over the shaft portion 104 of the proximal femur plate 100, between adjacent pairs of offset holes 106. The locking attachment plate 200 includes a body portion 206, sized and shaped to be mounted over the proximal portion 108 of the proximal femur plate 100, along with a first laterally extending wing 208 and/or a second laterally extending wing 210 extending therefrom. Each of the first and second laterally extending wings 208, 210 includes bone fixation element receiving openings 212, 214 extending therethrough, respectively. As will be described in greater detail below, the locking attachment plate 200 may be useful for cases in which additional fixation of the proximal femur plate 100 is desired and/or where the proximal femur plate 100 must accommodate larger portions of the stem or other prosthetic.

The body portion 206 is sized and shaped to be mounted or seated over a surface of the shaft portion 104 of the proximal femur plate 100 which, in an operative position, faces away from the bone. In particular, the body portion 210 may has a substantially bracket-like shape which, in the operative position, extends along the surface of the proximal femur plate 100 and over the longitudinal edges 130, 132. The body portion 206 may further include a body opening 224 extending therethrough. A connecting screw or other fixation element maybe inserted through the body opening 224 and one of the locking attachment openings 134 of the proximal femur plate 100 to couple the locking attachment plate 200 to the proximal femur plate 100 in a desired position therealong. As described above, a length of the body portion 206 (i.e., a distance between the proximal and distal ends 202, 204 thereof) corresponds to a distance between adjacent pairs of offset holes 106.

First and second laterally extending wings 208, 210 extend from first and second longitudinal sides 212, 214 of the body portion 206, respectively. Those skilled in the art will understand that these wings 208, 210 may be contoured (e.g., bent) by a user to better fit a patient's anatomy. Thus, in the operative position, the first and second laterally extending wings 208, 210 extend laterally beyond the longitudinal edges 130, 132 of the proximal femur plate 100 to contact the bone. Each of the first and second laterally extending wings 208, 210 includes bone fixation element receiving openings 216, 218, extending therethrough. In one embodiment, each of the first and second wings 208, 210 includes two bone fixation element receiving openings 216, 218. Preferably, two bone fixation elements may be inserted through the openings 216, 218 at a diagonal relative to one another—a first fixation element through one of the openings 216 extending through the first wing 208 and a second fixation element through one of the openings 218 extending through the second wing 210—such that the bone fixation elements are staggered along a length of the bone. Similarly to the offset holes 106 of the proximal femur plate 100, this may be done to prevent stress risers. In one embodiment, the bone fixation element receiving openings 216, 218 may be configured as variable angle holes.

Connecting portions 220 of the locking attachment plate 200 connecting the body portion 206 with the first and/or second wings 208 may include grooves 22 extending therealong so that, the first and second wings 208, 210 may be bent relative to the body portion 206 to adjust the attachment plate 200 to a specific patient's bone. As noted above, the first and second wings 208, 210 should come into contact with the bone when the proximal femur plate 100 and locking attachment plate 200 assembly is positioned along the bone.

Since the first and second wings 208, 210 extend beyond the longitudinal edges 130, 132 of the proximal femur plate, the locking attachment plate 200 may be particularly useful for situations in which the proximal femur plate 100 must be fixed to a portion of bone having a large portion of the stem of the prosthetic extending therethrough. In other words, a distance between the openings 216, 218 is greater than a distance between the first and second holes 110, 112 of the pair of offset holes 106 to accommodate a larger portion of the stem. Alternatively or, in addition, the locking attachment plate 200 may be used to provide fixation in addition to the fixation provided by the pairs of offset holes 106.

Figure 6:
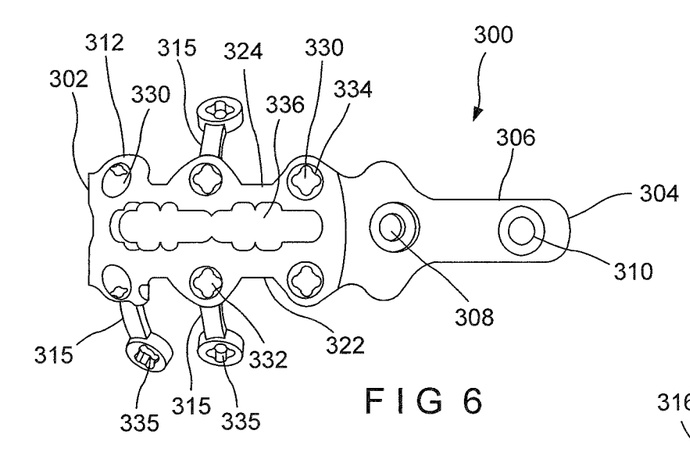
FIG. 6 shows a top plan view of a greater trochanteric attachment plate coupleable to the proximal femur plate of FIG. 1, according to a first exemplary embodiment of the present disclosure.
Figure 7:
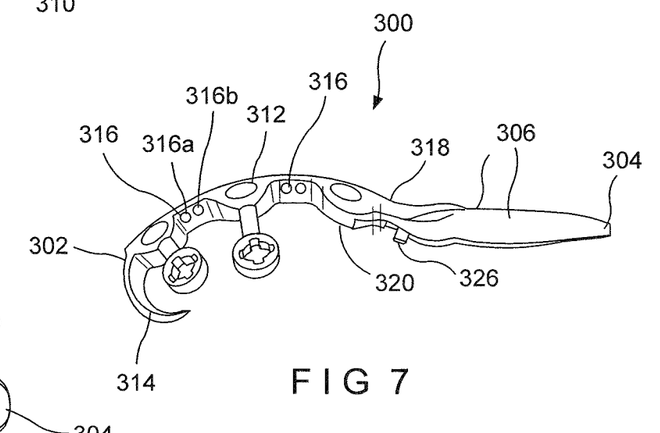
FIG. 7 shows a longitudinal side view of the greater trochanteric attachment plate of FIG. 6.
Figure 8:
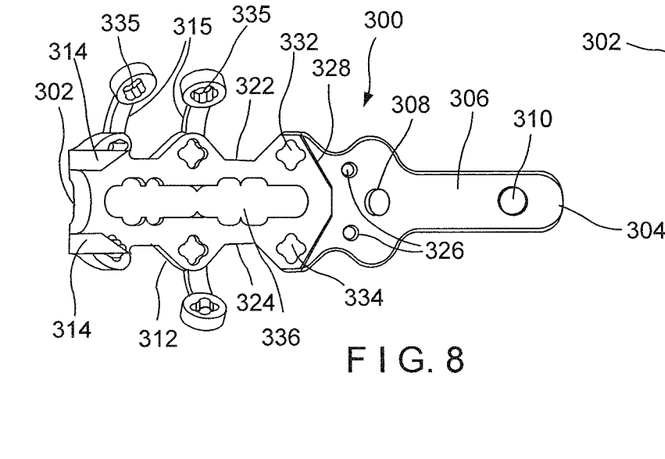
FIG. 8 shows a bottom plan view of the greater trochanteric attachment plate of FIG. 6.

As shown in FIGS. 6-8, the GT attachment plate 300 is configured to be attached to the head portion 102 of the proximal femur plate 100 to treat fractures of the greater trochanter. The GT attachment plate 300 extends along a longitudinal axis from a proximal end 302 to a distal end 304. The GT attachment plate 300 includes a distal portion 306 having a first connecting opening 308 and a second connecting opening 310 via which the GT attachment plate 300 is to be coupled to the proximal femur plate 100 via the connecting screws 350, as shown in FIGS. 9-11. Although, the GT attachment plate 300 is described as fixed to the plate 100 in a fixed position via connecting screws 350, those skilled in the art will understand that the position of the GT plate 300 relative to the plate 100 may be made adjustable (e.g., by providing a plurality of connection points on either the GT plate 300 or the plate 100, by including elongated holes within which the connecting screws may be mounted, etc.). A proximal portion 312 extends along a curve corresponding to a curve of a portion of the greater trochanter over which it is to be positioned so that, when the GT attachment plate 300 is assembled with the proximal femur plate 100, the proximal portion 312 extends proximally from the proximal end 114 of the proximal femur plate to extend along the greater trochanter. The proximal end 302 includes a pair of hooks 314 configured to engage a superior ridge at a proximal end of the greater trochanter. The GT attachment plate 300 may be fixed to the greater trochanter via bone fixation elements inserted through one or more holes of pairs of holes 330 extending through the proximal portion 312 and/or cables inserted through cable holes 316 extending through the proximal portion 312.

The GT attachment plate 300 is defined via a first surface 318 which, when the GT attachment plate 300 is in an operative position on the bone, faces away from the bone, and a second surface 320 which, when the GT attachment plate 300 is in the operative position on the bone faces the bone. The first and second surfaces 318, 320 are connected to one another via longitudinal side surfaces 322, 324. As described above, the GT attachment plate 300 is connected to the proximal femur plate 100 by laying the distal portion 306 over the proximal femur plate 100 so that the first connecting opening 308 and the second connecting opening 310 are aligned with the first GT attachment opening 128 and the second GT attachment opening 138, respectively. When the openings 308, 128 and 310, 138 have been aligned, connecting screws 350 which may be captive in the GT attachment plate 300 may be threaded into the proximal femur plate 100. Alternatively, connecting screws may be inserted into openings in the GT attachment plate 300 to couple to the plate 300 to the femur plate 100.

The GT attachment plate 300 and the proximal femur plate 100 may additionally include corresponding features for aiding alignment and providing rotational resistance. For example, the GT attachment plate 300 may include a pair of positioning pins 326 protruding from the second surface 320 to be received within correspondingly sized, shaped and positioned positioning openings 144 of the proximal femur plate 100, when the distal portion 306 is overlaid with the proximal femur plate 100, in proper alignment therewith. The GT attachment plate 300 may also include a shoulder 328 extending along the second surface 320 so that, when the GT attachment plate 300 is properly aligned with the proximal femur plate 100, the shoulder abuts the proximal end 114 of the proximal femur plate 100. This shoulder 328 is sized, shaped and positioned along the second surface 320 to correspond to the proximal end 114. Thus, when the shoulder 328 and the positioning pins 326 engage the proximal end 114 and the positioning openings 144, respectively, the GT attachment plate 300 is properly aligned with the proximal femur plate 100 and is prevented from being rotated relative thereto.

As described above, the GT attachment plate 300 may be attached to the proximal femur plate 100 using connecting screws 350, as shown in FIGS. 9-11. Each connecting screw 350 includes a head portion 352 and a shaft portion 354 extending therefrom. The shaft portion includes a unthreaded portion 356 immediately adjacent to the head portion 352 and a threaded portion 358 extending therefrom. The head portion 352 includes a recess 360 for receiving a correspondingly sized and shaped portion of a driving device, as will be understood by those of skill in the art. Once the GT attachment plate 300 and the proximal femur plate 100 have been aligned, as described above, a first connecting screw 350 is driven through the first connecting opening 308 and the first GT attachment opening 128 until the head portion 352 abuts the first surface 318 of the attachment plate 300. The unthreaded portion should reside within the first connecting opening 308 while the threaded portion engages a corresponding threading of the first GT attachment opening 128. Similarly, a second connecting screw 350 is inserted through the second connecting opening 310 and the second GT attachment opening 138 until the head portion 352 abuts the first surface 318 and the unthreaded portion 356 resides within the second connecting opening 310 while the threaded portion 358 engages the correspondingly threaded second GT attachment opening 138. As described above, the connecting screws 350 may be driven into the corresponding openings via a driving device received within the recess 360.

As described above, when the assembly of the GT attachment plate 300 and the proximal femur plate 100 is placed in a desired position along the femur, the proximal portion 312 of the GT attachment plate 300 extends along the greater trochanter. Thus, the proximal portion 312 extends along a curve corresponding to the shape of the underlying portion of the greater trochanter. The proximal end 302 includes the pair of hooks 314 for engaging the greater trochanter along with pairs of holes 330 and cable holes 316 for providing fixation.

Each of the hooks 314 curves from the proximal end 312 toward the distal end 304 of the GT attachment plate 300 so that, in the desired position on the bone, each of the hooks 314 engages a superior ridge of the greater trochanter. As would be understood by those skilled in the art, the hooks 314 may differ in length and/or radius of curvature to accommodate asymmetry in the structure of the underlying portion of the greater trochanter. The GT attachment plate 300 includes two hooks 314 so that the hooks 314 do not interfere with any portion of the prosthetic. In particular, one of the hooks 314 extends anterior relative to the prosthetic while the other of the hooks extends posterior relative to the prosthetic.

Pairs of holes 330 extend through the proximal portion 312 from the first surface 318 to the second surface 320. Each of the pairs of holes 330 includes a first hole 332 on a first side of a longitudinal axis of the GT attachment plate and a second hole 334 on a second side of the longitudinal axis opposite the first side so that bone fixation elements inserted through the first hole 332 and the second hole 334 may extend anterior and posterior to the prosthetic. The first and second holes 332, 334 of each pair of holes 330 may be substantially aligned along a length of the GT attachment plate 300. Similarly to the pairs of offset holes 106 of the proximal femur plate, the first and second holes 332, 334 may extend beyond longitudinal edges of the GT attachment plate 300. In one embodiment, a central axis along which each of the first and second holes 332, 334 extend may be substantially aligned with the longitudinal edges. The first and second holes permit placement of bone fixation elements anteroinferior and posteroinferior of the prosthetic towards a calcar of the femur. The first and second holes 332, 334 may be configured as variable angle holes so that bone fixation elements may be inserted therein at an angle relative to the central axes within a permitted range of angulations. It will be understood by those of skill in the art, however, that one or more of the first and second holes 332, 334 of each of the pairs of holes 330 may have a different configuration for receiving bone fixation elements. In one embodiment, the proximal portion 312 may include three pairs of holes 314. The number of pairs of holes 314, however, may vary.

The GT attachment plate 300 may further include one or more extension tabs 315 extending laterally from a portion of proximal portion 312 including the first and second holes 332, 334. In one particular embodiment, each extension tab 315 may extend substantially perpendicular relative to the longitudinal axis of the GT attachment plate 300. Each extension tab 315 includes an opening 335 extending through an end thereof for receiving a bone fixation element. The opening 335 may be similarly configured as a variable angle hole. A number of extension tabs 315 may vary, depending on a desired fixation of the GT attachment plate 300 and/or an anatomy of the greater trochanter over which the GT attachment plate 300 is to be placed. The extension tab 315 may be bent, as desired, to fit the patient's specific anatomy.

The proximal portion 312 may also include pairs of cable holes 316, each hole 316a, 316b being sized and shaped to receive a portion of a cable therein. Each of the holes 316a, 316b of the pair of cable holes 316 extends through the proximal portion 312 from a first longitudinal side surface 322 to a second longitudinal side surface 324. Each pair of cable holes 316 extends between adjacent pairs of holes 330 so that placement of cables do not interfere with a placement of bone fixation elements through holes 332, 334 of pairs of holes 330. As will be understood by those of skill in the art, a cable may be circled about a proximal end of the femur so that portions of the cable are received within the first and second cable holes 316a, 316b. The cable is tensioned and the ends of the cable are fixed relative to GT attachment plate 300 via, for example, a crimp, to fix the GT attachment plate 300 to the bone and/or provide fixation of the greater trochanter. The proximal portion 312 may include an elongated opening 336 extending therethrough, from the first surface 318 to the second surface 320 along the longitudinal axis of the GT attachment plate 300 for accommodating crimps for fixing the cable therewithin. In particular, the elongated opening 336 is in communication with the cable holes 316a, 316b so that a cable passing through the first and second cable holes 316a, 316b must also pass laterally through the elongated opening 336. A cable may be circled about the proximal end of the femur (e.g., to extend about a lesser trochanter of the femur) so that portions of the cable extend through the first and second holes 316a, 316b passing laterally through the elongated opening 336. A crimp received within the elongated opening 336 may be crimped over portions of the cable passing through the elongated opening 336 to maintain the cable in a tensioned configuration. The crimp may reside within the elongated opening 336 so that no portion of the crimp protrudes substantially beyond the first surface 318. In an exemplary embodiment, the proximal portion includes two pairs of cable holes 316.

Figures 12, 13:
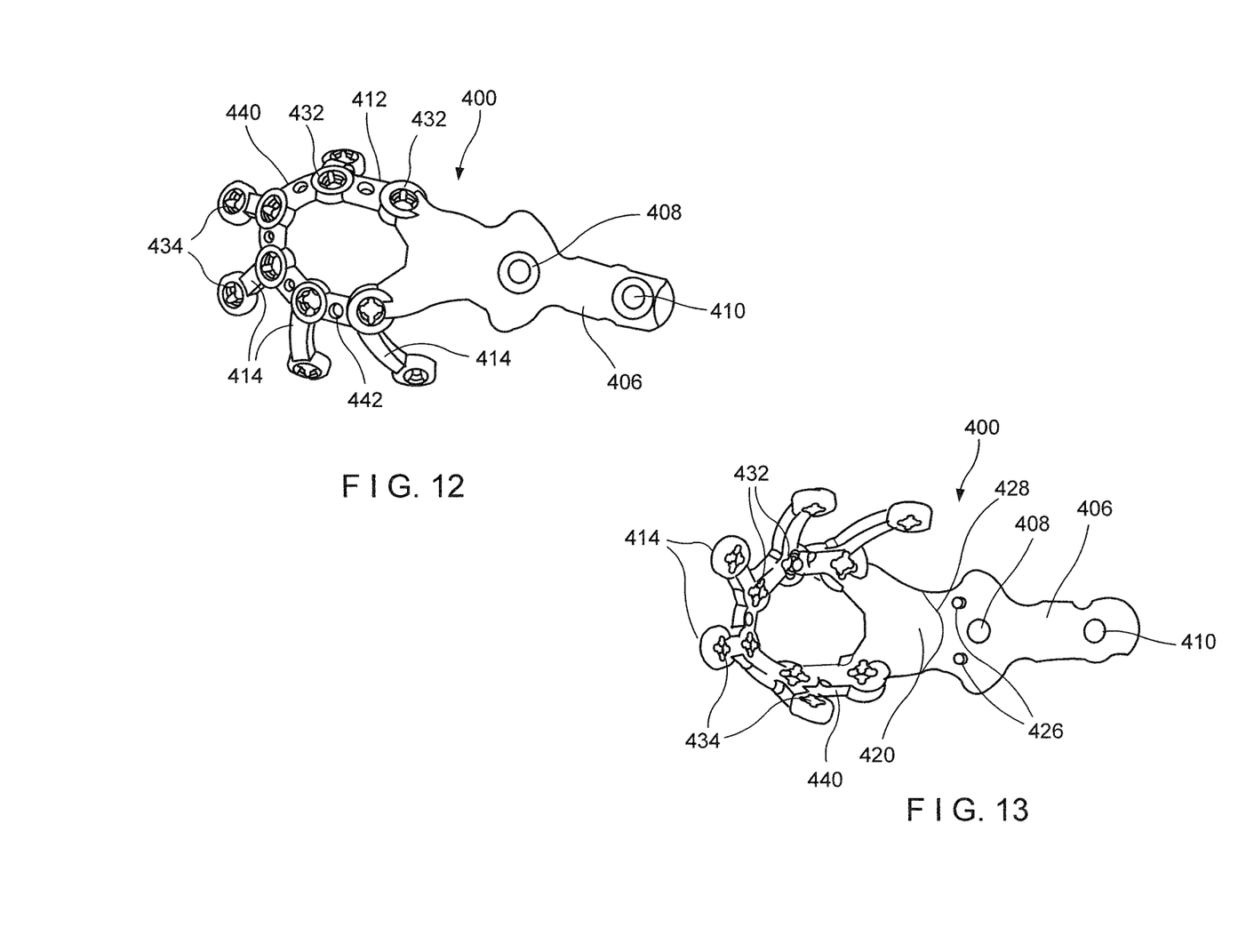
FIG. 12 shows a perspective view of a greater trochanteric attachment plate coupleable to the proximal femur plate of FIG. 1, according to a second exemplary embodiment of the present disclosure.
FIG. 13 shows another perspective view of the greater trochanteric attachment plate of FIG. 12.

As shown in FIGS. 12-13, a GT attachment plate 400 according to another exemplary embodiment may be similarly assembled with the proximal femur plate 100 to be positioned over the greater trochanter of the femur. Similarly to the GT attachment plate 300, the GT attachment plate 400 comprises a distal portion 406 for connecting the GT attachment plate 400 to the proximal femur plate 100 and a proximal portion 412 for placement over the greater trochanter. The distal portion 406 is substantially similar to the distal portion 306 and may be similarly attached to the proximal femur plate using the connecting screws 350 inserted through first and second connecting openings 408, 410 thereof which align with the first and second GT attachment openings 128, 138, respectively, of the proximal femur plate 100. Similarly to the GT attachment plate 300, a position of the GT attachment plate 400 relative to the plate 100 may be made adjustable (e.g., by providing a plurality of connection points on either the GT attachment plate 400 or the plate 100, by including elongated holes within which the connecting screws 350 may be mounted, etc.). The GT attachment plate 400 may also include similar alignment features such as, for example, positioning pins 426 protruding from a surface 420 of the GT attachment plate 400 facing toward the bone, in an operative position, and/or a shoulder 428 extending along the second surface 420. The positioning pins 426 and the shoulder 428 may engage the openings 144 and the proximal end 114, respectively, of the proximal femur plate 100.

Rather than extending along the greater trochanter and engaging the greater trochanter via hooks at a proximal end thereof, however, the proximal portion 412 includes a substantially ring-shaped portion 440 configured to be seated over the greater trochanter with the central opening of the ring-shaped portion positioned to avoid regions of the trochanteric bursa specifically where tendons connect to the bone and a plurality of extension tabs 414 extending radially therefrom. Each of the extension tabs 414 and the ring-shaped portion 440 include a bone fixation element receiving hole extending therethrough for fixing the GT attachment plate 400 to the bone. The ring-shaped portion 440 is sized and shaped to be seated over the greater trochanter and includes a plurality of first holes 432 extending therethrough. In one embodiment, the first holes 432 may be equidistantly spaced about the ring-shaped portion 440. The first holes 432 may be configured as variable angle holes for receiving bone fixation elements therein at desired angles relative to central axes along which the first holes extend. In the example shown, the ring-shaped portion includes six (6) first holes 432. It will be understood by those of skill in the art, however, that the number of first holes 432 may be varied depending on a size of the ring-shaped portion 440. The GT attachment plate 400 may be manufactured in a variety of sizes having different sizes of ring-shaped portion 440 so that a GT attachment plate 400 suited to a patient's specific anatomy may be selected.

The ring-shaped portion 440 may also include a plurality of suture holes 442 extending therethrough. Each suture hole 442 may be positioned between two adjacent first holes 432 and may extend through a portion of the ring-shaped portion 440 having an undercut so that the ring-shaped portion 440 may be sutured to surrounding tissue via the suture holes 442.

The extension tabs 414 extend radially away from the ring shaped portion 440, each extension tab 414 including a second hole 434. The extension tabs 414 may be bent, as desired, to fit the patient's specific anatomy. Each extension tab 414 may extend from a portion of the ring-shaped portion 440 including the first opening 432. An extension tab 414 is not required to extend from each of the first openings 432, however, depending on an anatomy over which the extension tabs 414 are desired to extend. The second holes 434 may be similarly configured as variable angle holes. In one embodiment, the GT attachment plate 400 includes five (5) extension tabs 414. It will be understood by those of skill in the art, however, that the number of tabs 414 may be varied depending on a size of the ring-shaped portion 440, a number of first holes 432 and/or an anatomy of the greater trochanter over which the GT attachment plate 400 is to be placed. The first and second holes 432, 434 of the GT attachment plate 400 permit insertion of bone fixation elements anteroinferior, posteroinferior and superior of the prosthetic towards a calcar of the femur.

According to an exemplary surgical method using the above-described system, a surgeon or other user may assess a type of periprosthetic fracture and a patient's specific anatomy to determine which plate 100, 200, 300 should be utilized. In some cases such as, for example, when a fracture extends only along a proximal shaft portion of the femur, the surgeon may determine that the proximal femur plate 100 may be utilized alone. In cases in which there are also fractures of the greater trochanter and/or where additional fixation is necessary, the surgeon may decide to use the proximal femur plate 100 along with the GT attachment plate 300 (or 400) and/or the locking attachment plate 200. The following method will describe the use of an assembly including all of the plates 100, 200 and 300. It will be understood by those of skill of the art, however, that the proximal femur plate 100 may be used alone, in a substantially similar manner.

Where more than one plate is being utilized, the plates should be assembled prior to implantation in the body. In particular, connecting screws 350 may be used to couple the distal portion 306 of the GT attachment plate 300 to the proximal femur plate 100, as described above. Similarly, a fixation element may be used to couple the locking attachment plate 200 along the proximal portion 108 of the shaft portion 104 of the proximal femur plate 100, between adjacent pairs of offset holes 106, as described above. Once the plates 100, 200 and 300 have been assembled, the assembly may be placed along the proximal femur such that the hooks 314 of the GT attachment plate 300 engage the superior ridge of the greater trochanter so that the proximal portion 312 of the GT attachment plate 300 extends along the greater trochanter and the proximal femur plate 100 extends distally therefrom along a length of the femur. In particular, the proximal end 114 of the proximal femur plate 100 should align with the vastus ridge of the greater trochanter.

Once the assembly has been positioned along the proximal femur, bone fixation elements may be inserted through desired ones of the first and second holes 108, 110 of the pairs of offset holes 106, first and second set of holes 122, 124, first and second bone fixation element receiving holes 216, 218 of the attachment plate 200, and first and second holes 332, 334 of the pairs of holes 330. As described above, all of these holes may be configured as 3.5 mm variable angle holes. Insertion of bone fixation elements through these holes permit insertion of bone fixation elements on an anterior and posterior side relative to the prosthetic. Bone fixation elements may be inserted through desired ones of the fixation holes 118 along the distal portion 116 of the proximal femur plate to provide fixation of the plate assembly distal of the prosthetic.

One or more cables may be inserted through the pairs of cable holes 316 to provide compression of greater trochanter. The cable may be circled and tensioned about the proximal end of the femur, a crimp residing within the elongated opening 336 crimped over the cable to maintain the cable in the tensioned configuration. While the cable(s) provide compression, bone fixation elements inserted through the first and second holes 332, 334 provide resistance to rotational and translational forces. Upon fixation of the plate assembly, as described, surrounding tissue may be sutured to the plate assembly via suture holes 316 and/or suture holes 126.

Figure 14:
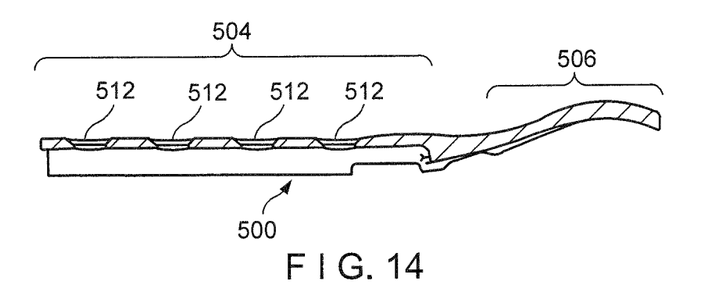
FIG. 14 shows a side view of a distal condylar plate according to an embodiment of the invention.
Figure 15:
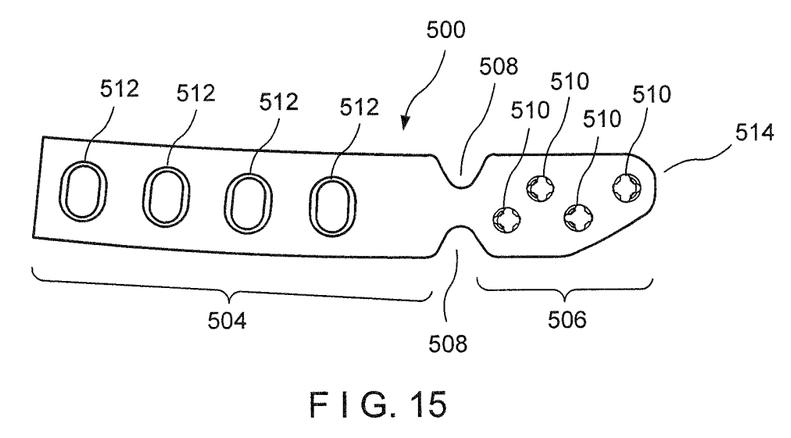
FIG. 15 shows perspective view of the distal condylar plate of FIG. 14.
Figure 16:
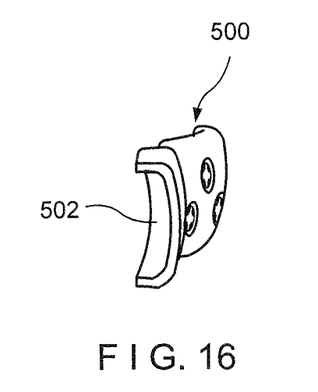
FIG. 16 shows a perspective view of the plate of FIGS. 14 and 15 from an end of the plate.

A condylar plate 500 according to an embodiment of the invention, as shown in FIGS. 14 and 15, is sized and configured to be attached to the distal end of a femoral plate such as the plate 100 of FIG. 1. Specifically, the plate 500 is designed to be mounted over the distal portion of a femoral plate such as the plate 100 to extend support from the distal end of the femoral plate distally to the femoral condyle to protect against secondary fractures as would be understood by those skilled in the art. Specifically, a bone facing side of the plate 500 forms a cavity 502 sized to receive a distal portion of a bone plate mounted to a femur. The plate 500 includes a shaft portion 504 and a head portion 506 separated from one another by gaps 508. As would be understood by those skilled in the art, the gaps 508 facilitate bending or otherwise contouring the plate 500 to more accurately suit the patient's anatomy so that the head portion 506 can follow as closely as possible the surface of the condyle to minimize irritation of surrounding tissues. As can be seen in FIG. 15, the head portion 506 includes several (in this embodiment 4) variable angle locking holes 510 each configured to receive a bone fixation element (e.g., a bone screw) therethrough to anchor the head portion 506 to the condyle. The shaft portion 504 of this embodiment includes 4 fixation element receiving holes 512 through any or each of which a bone fixation element may be inserted to pass into the bone via a hole in the underlying bone plate. For example, when the plate 500 is mounted as desired over a bone plate such as the plate 100, any or all of the holes 512 may align with one or more of the combination holes 118 of the plate 100. As would be understood by those skilled in the art, the head portion 506 is preferably shaped to minimize the footprint of the plate 500 on the condyle while providing a desired number of bone fixation element receiving holes (in this embodiment 4 variable angle locking holes). As would be understood by those skilled in the art, this condylar plate 500 may, if desired, be mounted over the proximal end of a femoral bone plate (if the proximal end of this femoral bone plate is sized and shaped similarly to the distal end of the plate 100) so that the head portion 506 may be mounted on the surface of the greater trochanter. As would be understood by those skilled in the art, the plates 500 may be shaped as mirror images with a first plate 500 shaped for mounting on a left distal condyle also suitable for mounting on a right greater trochanter and a second plate 500 being shaped for mounting on a right distal condyle that may also be mounted over a proximal portion of a femoral plate to extend to a left greater trochanter.

Although not described in detail, it will be understood by those of skill in the art that the plate assembly may utilize the GT attachment plate 400 in place of the GT attachment plate 300, depending on a desired fixation configuration of the greater trochanter. The GT attachment plate 400 may be assembled with the proximal femur plate 100 and utilized in a manner substantially similar to the method described above.

It will be understood by those of skill in the art that modifications and variations may be made in the structure and methodology of the present invention, without departing from the spirit or scope of the invention. Thus, it is intended that the present invention cover the modification and variations of this invention, provided that they come within the scope of the appended claims and their equivalents.

What is claimed is:

1. A system for treating a periprosthetic fracture, comprising:
   a periprosthetic bone plate including a head portion and a shaft portion extending longitudinally therefrom, the shaft portion including pairs of offset holes extending therethrough from a first surface of the periprosthetic bone plate which, in an operative position faces away from a bone, and a second surface which, in the operative position faces toward the bone, each of the pairs of offset holes including a first hole positioned on a first side of a longitudinal axis of the periprosthetic bone plate and a second hole positioned on a second side of the longitudinal axis opposite the first side so that bone fixation elements inserted therethrough extend anterior and posterior of a prosthetic received within the bone, the first and second holes offset relative to one another along a length of the shaft portion and extending beyond longitudinal edges of the shaft portion, the shaft portion further including a locking attachment opening positioned along the longitudinal axis and between a first pair of offset holes and an adjacent second pair of offset holes separated from the first pair of offset holes along the longitudinal axis; and
   a locking attachment plate including a body portion and a pair of wings extending laterally from the connecting portion, the body portion having a proximal end and a distal end and is sized and shaped to be mounted over the shaft portion of the periprosthetic plate with the locking attachment opening such that both the proximal end and the distal end of the body portion are disposed between the first pair of offset holes and the adjacent second pair of offset holes wherein the wings extend beyond the longitudinal edges of the shaft portion in the operative position and a first one of the wings includes a first pair of laterally outermost holes on the first side of the longitudinal axis and a second one of the wings includes a second pair of laterally outermost holes on the second side of the longitudinal axis,
   wherein the locking attachment plate includes a first locking attachment plate surface which, in an operative position faces away from the bone, a second locking attachment plate surface which, in the operative position faces toward the bone, and a thickness measured between the first locking attachment plate surface and the second locking attachment plate surface, the locking attachment plate including a connecting portion between the body portion and at least one of the wings, the connecting portion extending from the proximal end to the distal end of the body portion and the connecting portion having a connecting portion thickness less than each of a body portion thickness and a wing thickness,
   wherein respective center points at the first locking attachment plate surface of the first and second pairs of laterally outermost holes of the first and second ones of the wings are all disposed longitudinally inward of both the proximal end and the distal end of the body portion of the locking attachment plate.

2. The system of claim 1, wherein the first one of the wings includes two first holes and the second one of the wings includes two second holes.

3. The system of claim 1, wherein the locking attachment opening extends through the periprosthetic bone plate from the first surface to the second surface thereof.

4. The system of claim 3, wherein the locking attachment plate includes an opening extending through the body portion, the opening of the locking attachment plate aligning with the locking attachment opening in the operative position so that a fixation element inserted through the opening of the locking attachment plate and the locking attachment opening couples the locking attachment plate to the periprosthetic plate.

5. The system of claim 1, further comprising a greater trochanter attachment plate configured to be coupled to the head portion of the periprosthetic plate, the greater trochanter attachment plate including a proximal portion which, when the greater trochanter attachment plate is attached to the head portion, extends proximally therefrom to extend over a greater trochanter of the bone, in the operative position, wherein, when coupled to the periprosthetic plate in the operative position, a first surface of the greater trochanter attachment plate faces away from the bone while a second surface thereof faces toward the bone.

6. The system of claim 5, wherein the proximal portion of the greater trochanter attachment plate includes a pair of hooks at a proximal end thereof, each of the pair of hooks extending from the proximal end along a curve directed in a distal direction.

7. The system of claim 6, wherein the proximal portion of the greater trochanter attachment plate includes a plurality of pairs of holes extending therethrough from the first surface of the greater trochanter attachment plate to the second surface of the greater trochanter attachment plate so that, when coupled to the periprosthetic plate in the operative position, a first hole of each of the pairs of holes extends through the proximal portion of the greater trochanter attachment plate on a first side of a longitudinal axis of the greater trochanter attachment plate and a second hole of each of the pair of holes extends through the proximal portion of the greater trochanter attachment plate on a second side of the longitudinal axis of the greater trochanter attachment plate.

8. The system of claim 6, wherein the proximal portion of the greater trochanter attachment plate includes a pair of cable holes which, when the greater trochanter attachment plate is coupled to the periprosthetic plate in the operative position, extend through the greater trochanter attachment plate from a first longitudinal side surface to a second longitudinal side surface, the proximal portion of the greater trochanter attachment plate including an elongated opening extending therethrough from the first surface to the second surface thereof in communication with the pair of cable holes so that, when a cable is inserted through the pair of cable holes, a crimp received within the elongated opening is crimpable over portions of the cable passing across the elongated opening.

9. The system of claim 5, wherein the proximal portion of the greater trochanter attachment plate includes a ring-shaped portion and a plurality of extension tabs extending radially therefrom, the ring-shaped portion and each of the plurality of extension tabs including bone fixation element receiving openings extending therethrough, the ring-shaped portion being sized and shaped to be mounted over the greater trochanter.

10. The system of claim 9, wherein the extension portions are bendable with respect to the ring-shaped portion.

11. The system of claim 9, wherein the ring-shaped portion includes a suture hole between adjacent bone fixation element receiving openings.

12. The system of claim 5, wherein the periprosthetic plate and the greater trochanter attachment plate include corresponding alignment features for aligning the greater trochanter attachment plate relative to the periprosthetic plate.

13. The system of claim 12, wherein the corresponding alignment features include a shoulder along a bone facing surface of the greater trochanter attachment plate which, when the greater trochanter attachment plate is aligned with the periprosthetic plate, abuts a proximal end of the head portion.

14. The system of claim 12, wherein the corresponding alignment features include a pair of positioning protrusions protruding from the second surface of the greater trochanter attachment plate so that, when the greater trochanter attachment plate is aligned with the periprosthetic plate, the positioning protrusions are received within corresponding openings along the first surface of the periprosthetic plate.

15. The system of claim 1, wherein the pairs of offset holes extend through a proximal portion of the shaft portion which, when in the operative position extends over a portion of the bone including a prosthetic, the shaft portion further including a distal portion including a plurality of fixation openings extending therethrough, the distal portion extending over a portion of the bone distal of the prosthetic.

16. The system of claim 1, wherein the head portion includes a first set of holes extending therethrough on the first side of the longitudinal axis and a second set of holes extending therethrough on the second side of the longitudinal axis.

17. The system of claim 1, wherein a proximal end of the head portion is curved to correspond to a vastus ridge of a greater trochanter of the bone.

18. The system of claim 1, wherein the first and second holes of each of the pairs of offset holes are variable angle holes, each variable angle hole configured to receive a bone fixation element therethrough along a desired angle relative to a central axis along which the variable angle hole extends.

19. The plate according to claim 1, further comprising a second locking attachment plate hole opening located along the longitudinal axis of the periprosthetic bone plate between the second pair of offset holes and an adjacent third pair of offset holes separated from the second pair of offset holes along the longitudinal axis of the periprosthetic bone plate.

20. The plate according to claim 1, wherein the first pair of offset holes is proximal of the second pair of offset holes, a distal one of the first and second holes of the first pair of offset holes is separated from a proximal one of the first and second holes of the second pair of offset holes along the longitudinal axis of the periprosthetic bone plate by a distance of at least a width of the locking attachment plate as measured between the proximal and distal ends of the body portion of the locking attachment plate.

* * * * *